US00PP26577P3

(12) United States Plant Patent
Lloyd

(10) Patent No.: US PP26,577 P3
(45) Date of Patent: Apr. 5, 2016

(54) *DAPHNE* PLANT NAMED 'SWEET AMETHYST'

(50) Latin Name: *Daphne odora*
Varietal Denomination: Sweet Amethyst

(71) Applicant: Evan David Lloyd, Ashhurst (NZ)

(72) Inventor: Evan David Lloyd, Ashhurst (NZ)

( * ) Notice: Subject to any disclaimer, the term of this patent is extended or adjusted under 35 U.S.C. 154(b) by 86 days.

(21) Appl. No.: 13/999,336

(22) Filed: Feb. 13, 2014

(65) Prior Publication Data

US 2015/0230379 P1 Aug. 13, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt

(57) ABSTRACT

A new cultivar of *Daphne* plant named 'Sweet Amethyst' that is characterized by a large number of light purple flowers that have a strong jasmine scent, a long flowering season and elliptic to obovate shaped green leaves.

2 Drawing Sheets

Botanical classification: *Daphne odora.*
Variety denomination: 'Sweet Amethyst'.

BACKGROUND OF THE INVENTION

The present invention relates to a new and distinct cultivar of *Daphne* plant botanically known as *Daphne odora* and hereinafter referred to by the cultivar name 'Sweet Amethyst'.

The new *Daphne* was discovered by the inventor in 2009 as a naturally occurring single branch mutation growing on an individual plant of *Daphne odora* 'Cameo' (not patented). The cultivar 'Sweet Amethyst' was discovered in a population of outdoor container grown *Daphne* 'Cameo' plants in a cultivated area of Ashhurst, New Zealand.

Asexual reproduction of the new cultivar 'Sweet Amethyst' first occurred by softwood cuttings in 2010 in Ashhurst, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Daphne* cultivar 'Sweet Amethyst'. These traits in combination distinguish 'Sweet Amethyst' as a new and distinct cultivar apart from other existing known varieties of *Daphne.*

1. *Daphne* 'Sweet Amethyst' exhibits a large number of light purple flowers with a strong jasmine scent.
2. *Daphne* 'Sweet Amethyst' exhibits a long flowering season.
3. *Daphne* 'Sweet Amethyst' exhibits elliptic to obovate shaped green leaves.

The closest comparison cultivar is the parent plant *Daphne* 'Cameo'. 'Sweet Amethyst' is distinguishable from 'Cameo' by the following characteristics:

1. *Daphne* 'Sweet Amethyst' exhibits light purple flowers. In comparison, the flowers of 'Cameo' are pink.

2. *Daphne* 'Sweet Amethyst' exhibits a longer flowering season than the flowering season of 'Cameo'.
3. *Daphne* 'Sweet Amethyst' exhibits flowers with a stronger scent than the scent of the flowers of 'Cameo'.

BRIEF DESCRIPTION OF THE DRAWING

The accompanying photographs illustrate the distinguishing traits of *Daphne* 'Sweet Amethyst'.

Figure 1:
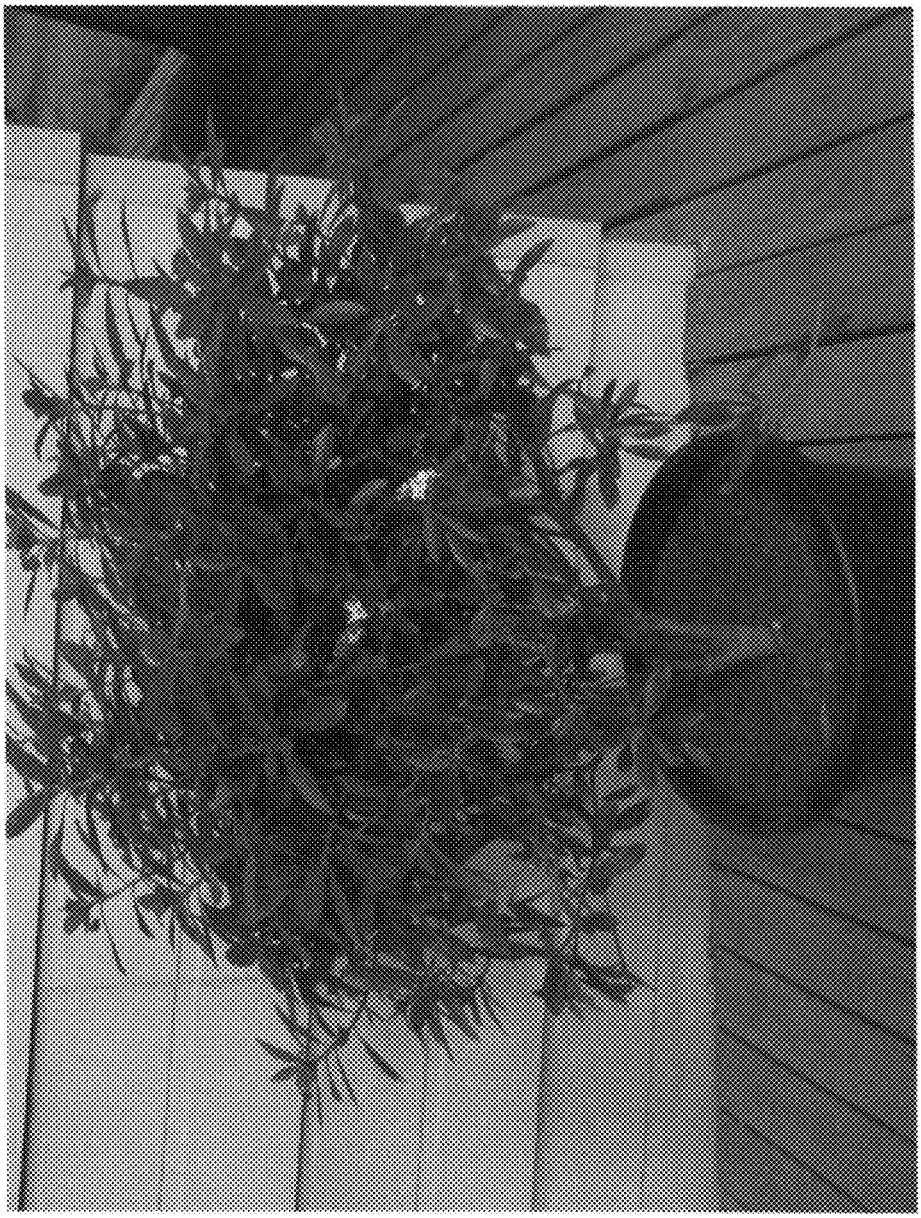
FIG. 1 shows an overall view of a 24 month old plant.
Figure 2:
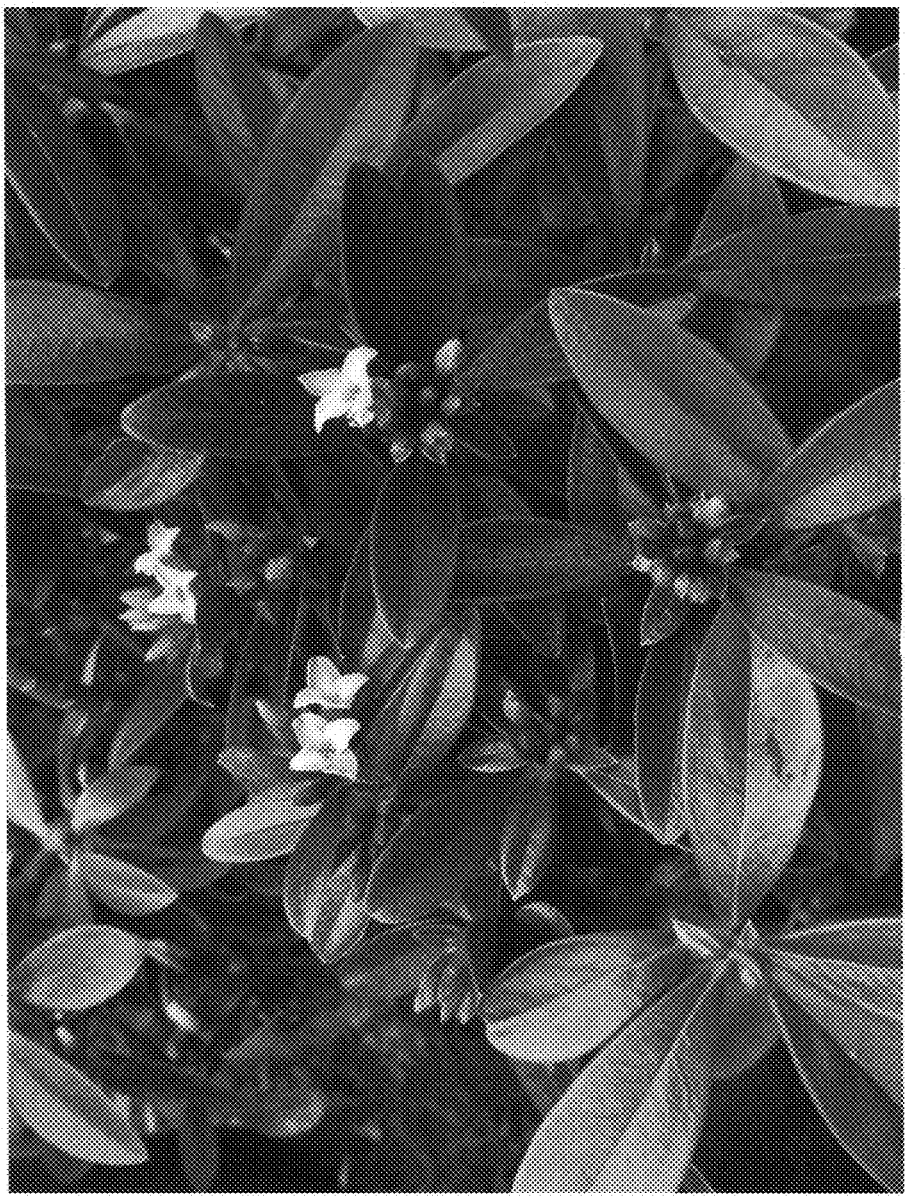
FIG. 2 shows an enlarged view of the flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Daphne* cultivar named 'Sweet Amethyst' Data was collected in Ashhurst, New Zealand from 24 month old outdoor field grown plants. The time of year was Summer in the Southern Hemisphere and the average temperature was 26 degrees Centigrade during the day and 18 degrees Centigrade at night. Color determinations are in accordance with The Royal Horticultural Society Colour Chart 2007 edition, except where general color terms of ordinary dictionary significance are used. The growing requirements are similar to the species. 'Sweet Amethyst' has not been tested under all possible conditions and phenotypic differences may be observed with variations in environmental, climatic, and cultural conditions, however, without any variance in genotype.

Botanical classification: *Daphne odora* 'Sweet Amethyst'.
Annual or perennial: Perennial.
Parentage: 'Sweet Amethyst' is a branch mutation of *Daphne* 'Cameo'.
Vigor: Moderate.
Growth habit: Upright and outwardly spreading.
Suitable container size: 3 liter.
Height: 50 cm. in height.

Diameter: 100 cm. in diameter.
Low temperature tolerance: −15° Centigrade.
High temperature tolerance: 35° Centigrade.
Propagation: Softwood cuttings and tissue culture.
Crop time: Approximately 2 years to produce a flowering plant.
Root system: Fine and fibrous.
Stem:
*Branching habit.*—Moderate branching.
*Average number of lateral branches.*—3 main lateral branches.
*Lateral branch dimensions.*—6 mm. in diameter and 18 cm. in length.
*Internode length.*—2 cm.
*Branch shape.*—Round.
*Branch texture.*—Smooth.
*Branch strength.*—Strong.
*Branch color.*—Young branches 144B, mature branches 200C.
*Pubescence.*—Absent.
Foliage:
*Foliage type.*—Evergreen.
*Leaf arrangement.*—Alternate.
*Compound or single.*—Single.
*Number of leaves per lateral branch.*—12 to 15.
*Leaf shape.*—Elliptic to obovate.
*Leaf apex.*—Mucronate.
*Leaf base.*—Cuneate.
*Leaf dimensions.*—8 cm. in length and 2 cm. in width.
*Texture.*—Glabrous on both surfaces.
*Pubescence.*—Absent.
*Leaf margin.*—Entire.
*Venation pattern.*—Pinnate.
*Young leaf color* (*upper surface*).—137B.
*Young leaf color* (*lower surface*).—137B.
*Mature leaf color* (*upper surface*).—146B.
*Mature leaf color* (*lower surface*).—146B.
*Vein color* (*upper surface*).—146B.
*Vein color* (*under surface*).—146B.
*Leaf attachment.*—Sessile.

Flower:
*Inflorescence arrangement.*—Terminal heads.
*Inflorescence dimensions.*—3.0 cm. in height and 3.5 cm. in width.
*Quantity of flowers per inflorescence.*—7 to 12.
*Natural flowering season.*—February to October in New Zealand.
*Fragrance.*—Strong jasmine scent.
*Bud dimensions.*—15 mm. in length and 10 mm. in diameter.
*Bud shape.*—Elliptic.
*Bud color.*—71C, tip N74C.
*Flower aspect.*—Outward and upward.
*Flower shape.*—Trumpet shaped flowers.
*Flower dimensions.*—10 mm. in width and 14 mm. in depth.
*Calyx.*—12 mm. in length.
*Tube dimensions.*—8 mm. in length and 2 mm. in diameter.
*Tube pubescence.*—Absent.
*Tube color.*—75A.
*Number of lobes.*—4 arranged in 2 whorls of 2.
*Lobe shape.*—Ovate.
*Lobe tip.*—Obtuse.
*Lobe margin.*—Entire.
*Lobe dimensions.*—8 mm. in length and 4 mm. in width.
*Lobe pubescence.*—Absent.
*Young lobe color* (*outer surface*).—N74D.
*Young lobe color* (*inner surface*).—N74D.
*Mature lobe color* (*outer surface*).—75A.
*Mature lobe color* (*inner surface*).—75A.
*Corolla.*—Absent.
*Self-cleaning or persistent.*—Self-cleaning.
Fruit and seed: Fruit and seed production have not been observed to date.
Disease and pest resistance: Disease and pest resistance has not been observed.

It is claimed:

1. A new and distinct variety of *Daphne* plant named 'Sweet Amethyst' as described and illustrated.

* * * * *